United States Patent [19]

Hauth

[11] 4,035,501

[45] July 12, 1977

[54] N-LYSERGYL-AMINO-PYRIDINES

[75] Inventor: Hartmut Hauth, Riehen, Switzerland

[73] Assignee: Sandoz Ltd., Basel, Switzerland

[21] Appl. No.: 589,372

[22] Filed: June 23, 1975

Related U.S. Application Data

[63] Continuation-in-part of Ser. No. 530,214, Dec. 6, 1974, abandoned, which is a continuation of Ser. No. 311,796, Dec. 4, 1972, abandoned.

[30] Foreign Application Priority Data

Dec. 10, 1971  Switzerland ..................... 18051/71
Dec. 10, 1971  Switzerland ..................... 18052/71

[51] Int. Cl.² ............... C07D 457/06; A61K 31/48
[52] U.S. Cl. ............................. 424/261; 260/285.5
[58] Field of Search ................ 260/285.5; 424/261

[56] References Cited

U.S. PATENT DOCUMENTS 2,997,470  8/1961  Pioch .............................. 260/285.5
3,904,633  9/1975  Karacsony et al. ............. 260/285.5

FOREIGN PATENT DOCUMENTS 125,347  1967  Czechoslovakia .............. 260/285.5

Primary Examiner—Donald G. Daus
Assistant Examiner—Mary C. Vaughn
Attorney, Agent, or Firm—Gerald D. Sharkin; Robert S. Honor; Thomas O. McGovern

[57] ABSTRACT

The present invention concerns heterocyclic compounds of the formula:

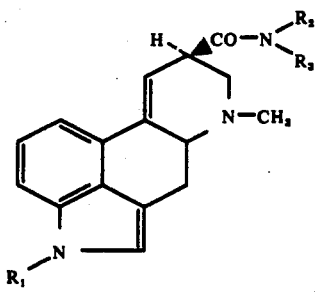

wherein $R_1$ is hydrogen or alkyl. $R_2$ is hydrogen or alkyl and $R_3$ is substituted or unsubstituted 3-pyridyl, which compounds are useful as salidiuretics and agents for migraine treatment.

18 Claims, No Drawings

N-LYSERGYL-AMINO-PYRIDINES

This application is a continuation-in-part of application Ser. No. 530,214 filed Dec. 6, 1974, now abandoned which in turn is a continuation of application Ser. No. 311,796 filed Dec. 4, 1972, now abandoned.

The present invention relates to heterocyclic compounds and more specifically to lysergic acid amide derivatives.

In accordance with the invention, there are provided compounds of formula I,

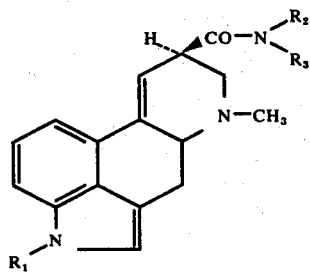

wherein $R_1$ is hydrogen or alkyl or 1 to 4 carbon atoms,
$R_2$ is hydrogen or alkyl of 1 to 4 carbon atoms, and
$R_3$ is 3-pyridyl, or 3-pyridyl substituted by alkyl of 1 to 4 carbon atoms, alkoxy of 1 to 4 carbon atoms, hydroxy, halogen of atomic number 9 to 53, amino, or monoalkylamino or dialkylamino, each alkyl substituent having 1 to 4 carbon atoms.

Further, in accordance with the invention a compound of formula I may be obtained by a process comprising
a. reacting a reactive functional derivative of an acid of formula II,

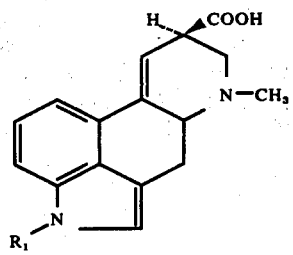

wherein $R_1$ is as defined above,
in an inert organic solvent in the presence of an acid-binding agent, with a compound of formula III,

wherein $R_2$ and $R_3$ are as defined above, or
b. reacting a compound of formula Ib,

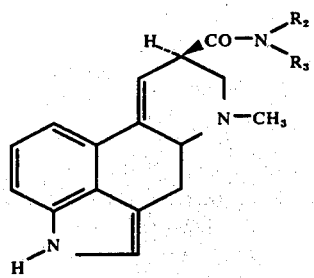

wherein $R_2$ and $R_3$ are as defined above,
in the presence of a strong base and in an inert organic solvent, with a halide of formula IV, $$R_1'-Hal \qquad IV$$

wherein $R_1'$ is alkyl of 1 to 4 carbon atoms,
and Hal is bromine or iodine,
to obtain a compound of formula Ia,

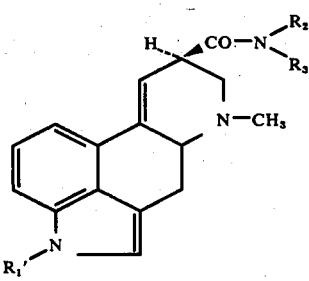

wherein $R_1'$, $R_2$ and $R_3$ are as defined above.

The compounds of formula I may exist in either free base or acid addition salt form. Acid addition salt forms may be obtained from free base forms in manner known per se and vice versa.

Substituted is preferably mono- or di-substituted. The substituents may be the same or different.

In process variant (a), the reactive functional derivative of an acid of formula II may be the reaction product obtained from the reaction of an acid of formula II with a chlorinating agent, e.g. thionyl chloride, phosgene, phosphorus oxychloride or oxalyl chloride, and an N-dialkyl substituted acid amide of an aliphatic monocarboxylic acid of 1 to 3 carbon atoms. However, other reactive derivatives of an acid of formula II may be used, e.g. the acid chloride hydrochloride, the acid azide, the addition product with carbodiimide or mixed anhydrides of an acid of formula II with sulfuric acid or trifluoroacetic acid.

Suitable inert organic solvents for the condensation reaction of the invention are, for example, chloroform, methylene chloride, acetonitrile and dimethyl formamide, and suitable acid-binding agents are tertiary amines, e.g. pyridine or triethylamine. The reaction is preferably effected at a temperature below room temperature, e.g. between about −30° and 5° C.

The reaction is preferably effected in the absence of moisture and employing absolute reagents.

The compounds of formula III are preferably used in free base form, but acid addition salt forms thereof may also be used. Process variant (a) is preferably effected by adding an acid of formula II to a suspension of dimethyl formamide and oxalyl chloride in an inert solvent, preferably acetonitrile, at −30° C. An inert atmosphere, e.g. nitrogen, may be employed. The reaction is generally independent of the rate of addition of the reagents. Stirring may be effected at −10° C for about 30 minutes, cooling may then be effected to −30° C, and a compound of formula III, dissolved in dimethyl formamide, may be added with the addition of an acid-binding agent, e.g. pyridine. The reaction mixture may be heated to 0° C and stirred, e.g. for about two further hours.

It is also possible in accordance with process variant a) to add a compound of formula III, in the presence of an acid-binding agent, such as triethylamine, to the acid chloride hydrochloride of the compound of formula II in an inert solvent, e.g. methylene chloride, conveniently at a temperature of from 0° to 5° C.

Working up of the resulting reaction mixture is effected by pouring the same on an ice-cold solution of sodium carbonate and extracting with methylene chloride. The compounds of formula I are isolated in known manner from the organic phase, in either free base or acid addition salt form thereof.

In accordance with process variant b), an alkali metal alcoholate or an alkali metal amide is preferably used as strong base.

A preferred method of effecting the alkylation process of the invention is by adding a compound of formula Ib to an alkali metal alcoholate. The alkali metal alcoholate may be suspended in liquid ammonia at e.g. −45° C. After dissolution, an alkyl halide of formula IV, e.g. an alkyl iodide, may be added dropwise, for example, in ether. Stirring for about one hour at −40° C may be effected.

A suspension of an alkali metal alcoholate may be prepared in situ, e.g. by adding portionwise metallic sodium or potassium to a solution of the corresponding alcohol such as methanol or ethanol, in liquid ammonia, and waiting for decolouration to occur.

About 2 to 5 mols of an alkali metal alcoholate and approximately the same of alkyl iodide are preferably used for every mol of a compound of formula Ib in the alkylation reaction.

Working up may be effected by pouring the reaction mixture into methylene chloride precooled e.g. to −40° C, covering the mixture with a layer of ice-cold saturated sodium hydrogen carbonate solution and removing the organic phase. The aqueous phase may be extracted with methylene chloride. The compounds of formula Ia are isolated in known manner from the combined organic phases.

In general, the free base forms of the compounds of formula I produced in accordance with the invention are crystalline at room temperature and with organic or inorganic acids form acid addition salt forms which are also crystalline at room temperature.

The compounds of formula I are useful because they possess pharmacological activity in animals. In particular, the compounds are useful as salidiuretics as indicated by standard tests e.g. the diuresis test in the rat and wake dog on p.o. administration of from 0.01 to 0.3 mg/kg animal body weight of the compound.

Compounds of formula Ia especially exhibit higher sodium excretion than potassium excretion.

For the abovementioned use, the dosage administered will of course vary depending on the compound employed, mode of administration and treatment desired. However, in general, satisfactory results are obtained when administered at a daily dosage of from 0.01 to 0.3 mg/kg animal body weight preferably given in divided doses 2 or 3 times daily, or in sustained release form. For the larger mammals, the total daily dosage is in the range of from about 1 to 40 mg and dosage forms suitable for oral administration contain from about 0.3 to 20 mg of the compound admixed with a pharmaceutical carrier or diluent.

Specific examples of daily dosages, at which satisfactory results are obtained, are:

i. N-(1-methyl-lysergyl)-3'-amino-pyridine, ...0.01 to 0.3 mg/kg animal body weight administered p.o.;

ii. N-(1-methyl-lysergyl)-5'-amino-2'-chloropyridine, ..0.01 to 0.3 mg/kg animal body weight administered p.o; and iii. N-(1-methyl-lysergyl)-5'-amino-2'-n-butoxypyridine, ...0.01 to 0.3 mg/kg animal body weight administered p.o.

The compounds of formula Ia are further useful as antiserotonin agents, e.g. in the treatment of migraine, as indicated by standard tests, e.g. by the in vitro serotonin toxicity test in the isolated rat uterus on administration by infusion of 0.8 mg/liter of the compound and in vivo serotonin antagonism test in the guinea pig on s.c. administration of from 0.1 to 1.0 mg/kg animal body weight of the compound.

For the abovementioned further use, the dosage administered will of course vary depending on the compound employed mode of administration and treatment desired. However, in general, satisfactory results are obtained when administered at a daily dosage of from about 0.01 to 1.0 mg/kg animal body weight, preferably given in divided doses 2 or 3 times daily, or in sustained release form. For the larger mammals, the total daily dosage is in the range of from about 1.0 to 10 mg and dosage forms suitable for oral administration contain from about 0.3 to 5 mg of the compound admixed with a pharmaceutical carrier or diluent.

Specific examples of daily dosages, at which satisfactory results are obtained, are:

i. N-(1-methyl-lysergyl)-3'-amino-pyridine, ...0.01 to 1.0 mg/kg animal body weight administered s.c.;

ii. N-(1-methyl-lysergyl)-5'-amino-2'-chloropyridine, ...0.01 to 1.0 mg/kg animal body weight administered s.c.; and iii. N-(1-methyl-lysergyl)-5'-amino-2'-n-butoxypyridine, ...0.01 to 1.0 mg/kg animal body weight administered s.c.

Pharmaceutically acceptable acid addition salt forms of the compounds of formula I exhibit the same order or activity as the free base forms. Examples of acids for pharmaceutically acceptable acid addition salt formation are organic acids such as maleic acid or tartaric acid, and inorganic acids such as hydrochloric acid or sulphuric acid.

For the abovementioned uses, the compounds of formula I may be employed in the form of a pharmaceutical composition. A pharmaceutical composition may comprise a compound of formula I, in free base or pharmaceutically acceptable acid addition salt form, in association with a pharmaceutical carrier or diluent. A suitable form of composition is a tablet or capsule.

Insofar as an acid addition salf form of a compound of formula I is not pharmaceutically acceptable such form may be used as an intermediate for the production of the free base form or pharmaceutically acceptable acid addition salt forms of the compound of formula I in manner known per se.

The compounds of formula Ib are useful as intermediates in the production of compounds of formula Ia in accordance with process variant b) hereinbefore described.

A preferred class of compounds of formula Ia are those wherein $R_3$ is 3-pyridyl or 3-pyridyl substituted by alkoxy of 1 to 4 carbon atoms, chlorine, bromine, or dialkylamino, for example wherein $R_3$ is 3-piperidyl or 3-piperidyl substituted by methoxy, n-butoxy, chlorine or dimethylamino. A preferred sub-class of compounds of formula Ia are the abovementioned compounds of formula Ia wherein $R_1$ is methyl and $R_2$ is hydrogen or methyl. An example of a preferred specific compound of formula I is N-(1-methyl-lysergyl)-3'-amino-pyridine.

In the following non-limitative Examples all temperatures are indicated in degrees Centigrade.

Insofar as the production of the starting materials is not described, these are known or may be produced in accordance with known processes, or in a manner analogous to known processes.

EXAMPLE 1

N-(1-Methyl-lysergyl)-3'-amino-pyridine[process a)]

A solution of 8.55 cc (100 millimols) of oxalyl chloride in 60 cc of absolute acetonitrile is slowly added dropwise at −30° to 150 cc of absolute dimethyl formamide and 300 cc of absolute acetonitrile in the absence of moisture and while passing through a stream of nitrogen. After 5 minutes 28.2 g (100 millimols) of anhydrous d-1-methyl-lysergic acid are added at the same temperature while stirring, and stirring is effected at −10° for 30 minutes. The reaction mixture is subsequently cooled to −30°, 50 cc of absolute pyridine are added and immediately thereafter 14.1 g (150 millimols) of 3-amino-pyridine, dissolved in 150 cc of dimethyl formamide, are added. After stirring at 0° for 2 hours, the reaction mixture is poured into 1 liter of ice-cold 10% soda solution and is extracted with methylene chloride. After washing with water, the organic phase is dried over sodium sulfate, concentrated and dried in a high vacuum at 50°. The crude product is chromatographed on a 50-fold quantity of basic aluminium oxide (activity II). The iso compound is removed with methylene chloride; N-(1-methyl-lysergyl)-3'-amino-pyridine is eluted with methylene chloride and 0.5% of methanol.

Maleate form: from acetone, M.P. 176°–178° (decomp.), $[\alpha]_D^{22} = -45° \pm 2°$ (c = 0.5, pyridine).

The following compounds may be obtained in a manner analogous to that described in Example 1 from lysergic acid:

| Ex. | Compound | M.P. | Specific rotation |
|---|---|---|---|
| 2 | N-lysergyl-3'-amino-pyridine in base form from acetone | 197–199° | $[\alpha]_D^{22} = -68° \pm 2°$ (c = 0.5, pyridine) |
| 3 | N-lysergyl-5'-amino-2'-n-butoxy-pyridine in hydrogen maleate form from methanol/acetone | 205–208° (decomp.) | $[\alpha]_D^{21} = +63°$ (c = 0.5, 50 % ethanol) |
| 4 | N-lysergyl-3'-amino-2',6'-dimethoxy-pyridine in hydrogen maleate form from methanol/acetone | 202–203° (decomp.) | $[\alpha]_D^{21} = +51°$ 0.5, 50 % ethanol) |
| 5 | N-lysergyl-5'-(N-methylamino)-2'-methoxy-pyridine in base form from methanol/ether | 207–209° | $[\alpha]_D^{21} = -127°$ (c = 0.5, pyridine) |
|  | in hydrogen maleate form from acetone/ether | 150–152° | $[\alpha]_D^{21} = -66°$ (c = 0.5, 50 % ethanol) |

EXAMPLE 6

N-Lysergyl-5'-amino-2'-chloro-pyridine[process a)]

A solution of 1.61 g (12.5 millimols) of 5-amino-2-chloro-pyridine, 3.5 cc (25 millimols) of triethylamine and 50 cc of absolute methylene chloride is added dropwise at 0°–5° within about 15 minutes to a suspension of 3.25 g (10 millimols) of d-lysergic acid chloride hydrochloride in 100 cc of absolute methylene chloride in the absence of moisture. The reaction mixture is stirred at the same temperature for 40 minutes, is then poured on ice and extracted with methylene chloride and a 2 N soda solution while cooling with ice. The methylene chloride phases are washed with water, dried and concentrated by evaporation.

The hydrogen maleate form is produced from the crude base form in the usual manner.

Hydrogen maleate form: from methanol, M.P. 200°–202° (decomp.), $[\alpha]_D^{21} = +60°$ (c = 0.50, 50% ethanol).

EXAMPLE 7

5'-(N-Lysergyl-amino)-2'-(dimethylamino)-pyridine[process a)]

The title compound is obtained in a manner analogous to that described in Example 6 by employing 5-amino-2-dimethylamino-pyridine instead of 5-amino-2-chloro-pyridine; the bis-hydrogen maleate form of the title compound has a M.P. of 174°–177° (decomp.) after crystallization from methanol/ether, $[\alpha]_D^{21} = +75°$ (c = 0.5, 50% ethanol).

The compounds analogous to Examples 2 to 6 alkylated in the 1-position of the lysergic acid structure may be produced by an analogous process to that described in Example 1.

EXAMPLE 8

N-(1-Methyl-lysergyl)-3'-amino-pyridine[process b)]

3.44 g (10 millimols) of d-N-lysergyl-3'-amino-pyridine are added portionwise at −45° to a suspension of 3.4 g (50 millimols) of sodium ethanolate in 100 cc of liquid ammonia. After stirring at −45° for 15 minutes, a solution of 7.1 g (50 millimols) of methyl iodide in 5 cc of ether is slowly added dropwise and stirring is effected at −40° for 1 hour. Working up is effected by carefully pouring into 300 cc of methylene chloride cooled to −40° and covering with a layer of about 200 cc of ice-cooled, saturated sodium hydrogen carbonate solution, while stirring. The aqueous phase is again extracted with methylene chloride, the combined organic phases are dried over sodium sulfate and concentrated by evaporation in a vacuum at a bath temperature of 40°. The maleate form of the title compound is produced from the resulting crude base in the usual manner.

Maleate form: from acetone, M.P. 176°–178° (decomp.), $[\alpha]_D^{22} = -45° \pm 2°$ (c = 0.5, pyridine).

The following compounds may be obtained in a manner analogous to that described in Exampkle 8 from the corresponding compounds of formula Ib.

| Ex. | Compound | M.P. | $[\alpha]_D^{21}$ (c = 0,5, 50 % ethanol |
|---|---|---|---|
| 9 | N-(1-methyl-lysergyl)-5'-amino-2'-chloro-pyridine in hydrochloride form from acetone/ether | from 220° (decomp.) | +62° |
| 10 | 5'-[N-(1-methyl-lysergyl)-amino]-2'-(dimethylamino)-pyridine in dihydrochloride form from methanol/ether | 218–219° (decomp.) | +55° |
| 11 | N-(1-methyl-lysergyl)-5'-amino-2'-n-butoxy-pyridine in hydrogen maleate form from methanol/acetone | 195–196° (decomp.) | +52° |
| 12 | N-(1-methyl-lysergyl)-3'-amino-2',6'-dimethoxy-pyridine in hydrogen tartrate form from acetone/ether | 110–112° | +64° |
| 13 | N-(1-methyl-lysergyl)-5'- | | |

| Ex. | Compound | M.P. | $[\alpha]_D^{21}$ (c = 0,5, 50 % ethanol) |
|---|---|---|---|
| from 170° | -continued (N-methylamino)-2'-methoxy-pyridine in hydrochloride form from methanol/acetone | (decomp.) | −36° |

In analogous manner to that described in Examples 8 to 13, the following compounds are produced viz:
N-(1-Methyl-lysergyl)-3'-amino-2',6'-dimethyl-pyridine,
N-(1-methyl-lysergyl)-5'-amino-2'-hydroxy-pyridine,
N-(1-methyl-lysergyl)-5'-amino-2'-fluoro-pyridine,
N-(1-methyl-lysergyl)-5'-amino-2'-bromo-pyridine,
N-(1-methyl-lysergyl)5'-amino-2'-iodo-pyridine,
5'-[N-(1-methyl-lysergyl)-amino]-2'-(amino)-pyridine, and
5'-[N-(1-methyl-lysergyl)-amino]-2'-(methylamino)-pyridine.

What is claimed is:
1. A compound of the formula:

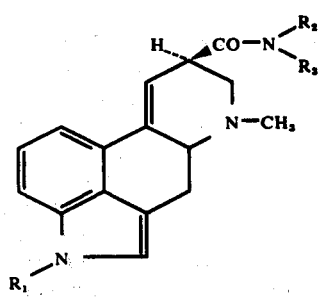

wherein R₁ is alkyl of 1 to 4 carbon atoms,
R₂ is hydrogen or alkyl of 1 to 4 carbon atoms, and
R₃ is 3-pyridyl, or 3-pyridyl mono- or di substituted by alkyl of 1 to 4 carbon atoms, alkoxy of 1 to 4 carbon atoms, hydroxy, halogen of atomic number 9 to 53, amino, or monoalkylamino or dialkylamino, each alkyl substituent having 1 to 4 carbon atoms,
in free base or acid addition salt form.

2. A compound of claim 1, in pharmaceutically acceptable acid addition salt form.

3. A compound of claim 1, wherein R₃ is 3-pyridyl-mono or di- 3-pyridyl substituted by alkoxy of 1 to 4 carbon atoms, chlorine, bromine or dialkylamino, each alkyl substituent thereof having 1 to 4 carbon atoms.

4. A compound of claim 3, wherein R₃ is 3-pyridyl or 3-pyridyl mono- or di- substituted by methoxy, n-butoxy, chlorine or dimethylamino.

5. A compound of claim 2, wherein R₁ is methyl.

6. A compound of claim 2, wherein R₂ is hydrogen or methyl.

7. The compound of claim 2, which is N-(1-methyl-lysergyl)-3'-amino-pyridine.

8. The compound of claim 2, which is N-(1-methyl-lysergyl)-5'-amino-2'-chloro-pyridine.

9. The compound of claim 2, which is 5'-[N-(1-methyl-lysergyl)-amino]-2'-(dimethylamino)-pyridine.

10. The compound of claim 2, which is N-(1-methyl-lysergyl)-5'-amino-2'-n-butoxy-pyridine.

11. The compound of claim 2, which is N-(1-methyl-lysergyl)-3'-amino-2',6'-dimethoxy-pyridine.

12. The compound of claim 2, which is N-(1-methyl-lysergyl)-5'-(N-methylamino)-2'-methoxy-pyridine.

13. A method of increasing sodium output in the urine flow of animals which comprises administering to an animal in need of such treatment a therapeutically effective amount of a compound of the formula:

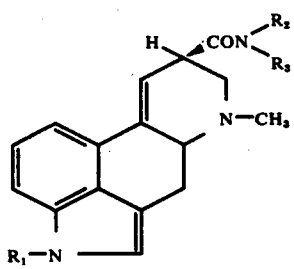

where R₁, R₂, and R₃ are as defined in claim 1 or a pharmaceutically acceptable acid addition salt thereof.

14. A method according to claim 13 in which 1 to 40 milligrams of the compound are administered daily.

15. A method according to claim 13 in which 0.3 to 20 milligrams of the compound are administered per unit dose.

16. A method according to claim 15 in which R₁ is methyl.

17. A method according to claim 16 in which the compound is N-(1-methyl-lysergyl)-5'-amino-2'-n-butoxy-pyridine.

18. A method of treating migraine in animals which comprises administering to an animal in need of such treatment a therapeutically effective amount of a compound of the formula:

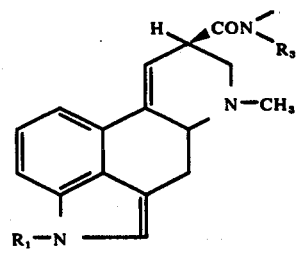

where R₁, R₂, and R₃ are as defined in claim 1 or a pharmaceutically acceptable acid addition salt thereof.

* * * * *